United States Patent
Felix et al.

(10) Patent No.: US 10,918,296 B1
(45) Date of Patent: Feb. 16, 2021

(54) FLEXIBLE ELECTROCARDIOGRAM (ECG) PADS

(71) Applicant: Vital Connect, Inc., Campbell, CA (US)

(72) Inventors: Charles Ian Felix, Los Gatos, CA (US); Steven E. Gauvin, Lovland, CO (US)

(73) Assignee: Vital Connect, Inc., San Jose, CA (US)

( * ) Notice: Subject to any disclaimer, the term of this patent is extended or adjusted under 35 U.S.C. 154(b) by 597 days.

(21) Appl. No.: 14/798,348

(22) Filed: Jul. 13, 2015

(51) Int. Cl.
*A61B 5/04* (2006.01)
*A61B 5/0408* (2006.01)

(52) U.S. Cl.
CPC .... *A61B 5/0408* (2013.01); *A61B 2562/0209* (2013.01); *A61B 2562/125* (2013.01)

(58) Field of Classification Search
CPC . A61B 5/04; A61B 2562/0215; A61B 5/6831; A61B 5/04085; A61B 5/0006
USPC ................................. 600/372, 382, 391–395
See application file for complete search history.

(56) References Cited

U.S. PATENT DOCUMENTS

| | | | | |
|---|---|---|---|---|
| 4,832,036 A * | 5/1989 | Cartmell | ............ | A61B 5/04087 600/396 |
| 6,434,410 B1 * | 8/2002 | Cordero | ............. | A61B 5/04085 600/396 |
| 2010/0081913 A1 * | 4/2010 | Cross | ................. | A61B 5/04085 600/386 |
| 2011/0077497 A1 * | 3/2011 | Oster | ................... | A61B 5/0002 600/372 |
| 2012/0190956 A1 * | 7/2012 | Connolly | ............. | A61B 5/0537 600/372 |
| 2013/0345539 A1 * | 12/2013 | Quintanar | .......... | A61B 5/04085 600/385 |
| 2015/0141791 A1 * | 5/2015 | O'Neill | ............. | A61B 5/04085 600/391 |

OTHER PUBLICATIONS

A. Cranny. Screen-printed potentiometric Ag/AgCl chloride sensors: Lifetime performance and their use in soil salt. Sensors and Actuators A 169 (Feb. 2011) 288-294.*

Brissette, Peter. Printed Circuit Board Finishes. Bay Area Circuits, Feb. 2012. https://bayareacircuits.com/printed-circuit-board-finishes/.*

Atkinson et al. "An investigation into the effect of fabrication parameter variation on the characteristics of screen-printed thick-film silver/silver chloride reference electrodes". Microelectronics International 28/2 (2011) 49-52.*

(Continued)

*Primary Examiner* — Joseph A Stoklosa
*Assistant Examiner* — Brian M Antiskay
(74) *Attorney, Agent, or Firm* — Brundidge & Stanger, P.C.

(57) ABSTRACT

A system and method for providing a flexible electrocardiogram (ECG) pad structure have been disclosed. In a first aspect, the system is the flexible ECG pad structure and comprises a copper layer and a paste trace layer coupled to the copper layer via a cover. In a second aspect, the method comprises providing a copper layer and coupling a paste trace layer to the copper layer via a cover.

15 Claims, 5 Drawing Sheets

(56) References Cited

OTHER PUBLICATIONS

Cranny et al. "Screen-printed potentiometric Ag/AgCI chloride sensors: Lifetime performance and their use in soil salt measurements". Sensors and Actuators A: Physical. 169 (2011) 288-294.*
Z-axis, Inc. "How to choose a surface finish for a PCB" Jun. 18, 2014 https://www.youtube.com/watch?v=wqTef_xfbel (Year: 2014).*
Bozkurt et al. "Low-cost flexible printed circuit technology based microelectrode array for extracellular stimulation of the invertebrate locomotory system". Sensors and Actuators A: Physical 169 (2011) 89-97 (Year: 2011).*

* cited by examiner

FLEXIBLE ELECTROCARDIOGRAM (ECG) PADS

FIELD OF THE INVENTION

The present invention relates to wearable sensor devices, and more particularly, to a flexible design for the electrocardiogram (ECG) pads of the wearable sensor devices.

BACKGROUND

Wearable sensor devices are utilized to continuously monitor health related parameters of a user. These wearable sensor devices can include a variety of sensor devices including but not limited to electrocardiogram (ECG) electrodes. Conventional wearable sensor devices utilize copper flex technology to provide the ECG electrode structures. When the wearable sensor devices come in contact with the user's body, the copper flex technology corrodes which creates cosmetic and shelf life issues. Therefore, there is a strong need for a cost-effective and efficient solution that overcomes the aforementioned issues. The present invention addresses such a need.

SUMMARY OF THE INVENTION

A system and method for providing a flexible electrocardiogram (ECG) pad structure have been disclosed. In a first aspect, the system is the flexible ECG pad structure and comprises a copper layer and a paste trace layer coupled to the copper layer via a cover.

In a second aspect, the method comprises providing a copper layer and coupling a paste trace layer to the copper layer via a cover.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
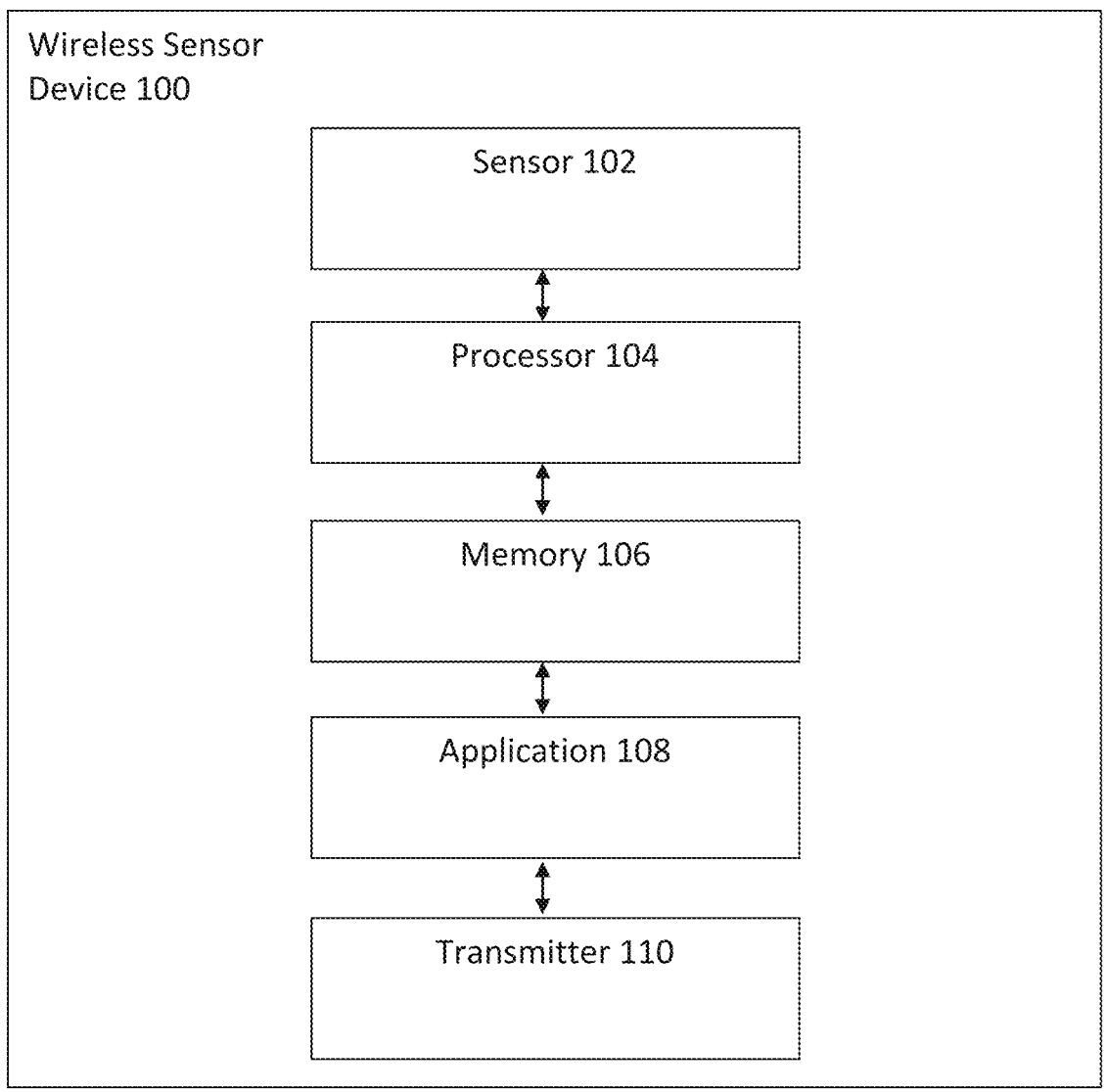
FIG. 1 illustrates a wireless sensor device that utilizes a flexible circuit design that includes a flexible ECG pad structure in accordance with an embodiment.

The present invention relates to wearable sensor devices, and more particularly, to a flexible design for the electrocardiogram (ECG) pads of the wearable sensor devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Wearable sensor devices utilize copper flex technology to provide the ECG electrode structures that enable the wearable sensor device to monitor the health of the user. The copper flex technology comprises a flexible circuit with a copper underlay that is in contact with the ECG structures and pads. In one embodiment, electrical contact to the body is made through the use of hydrogel (including but not limited to a polymerized salt water solution) that has a high sodium ion content. Sodium ions are well known for their high mobility and once they come in contact with the copper, they cause a chemical reaction or corrosion that results in copper(II) chloride (CuCl2).

The CuCl2 is non-hazardous to the user/patient but creates a cosmetic issue by discoloring the wearable sensor device (e.g., the wearable sensor devices pads can turn green) and also creates shelf-life issues by degrading the connection with the electrodes which can result in less accurate information.

In one embodiment, the wearable sensor device utilizes barrier layers or overlays (including but not limited to electroless nickel immersion gold (ENIG), polyisocyanurate (PIC), and silver chloride (AgCl)) on the ECG pad portion that comprises the copper flex technology to provide good conductance and protection of the copper contact and interconnect traces of the copper flex technology. However, the barrier layers that are added are thin and thus susceptible to cracking through the mishandling of the product during the manufacturing process or during normal wear and usage of the device (i.e., when the flexible circuit moves as the user wears it) which could still result in CuCl2.

In another embodiment, the ECG pads are made with a tin rivet that is covered with silver/silver chloride (Ag/AgCl) and has a hydrogel layer applied on top. In this embodiment, there is no chemical reaction that creates CuCl2 because there is no copper in the ECG pads construction and design. However, the tin rivet construction can only be utilized in a wired construction and cannot be utilized in a wearable sensor device that is in a wireless patch construction and form factor. In addition, maintaining the usage of copper in the flex design enables optimized electrical connections to be created.

A method and system in accordance with the present invention provides a wearable sensor device with a flexible ECG pad structure that eliminates the occurrence of the CuCl2 chemical reaction (corrosion) thereby mitigating cosmetic and shelf life issues. The flexible ECG pad structure utilizes a polyimide based flex technology and design that eliminates hydrogel ion migration to the copper portion of the flexible ECG pad structure by creating a silver paste contact and trace construct in place of the copper contact and trace construct. The polyimide provides a base that the flex circuit and associated flexible ECG pad structure are built on top of. In another embodiment, different materials other than silver are utilized to create the contact and trace construct including but not limited to gold (Au) and impregnated or activated carbon.

In one embodiment, the flexible ECG pad structure with a silver paste contact and trace construct is provided by applying an ENIG land or cover on a first portion of the copper trace layer of the flexible ECG pad structure that is outside of the hydrogel area and on a top layer of the flexible ECG pad structure. After the ENIG cover is applied, a cover layer is also applied on a second portion of the copper trace layer of the flexible ECG pad structure. In one embodiment, the first and second portions make up the entire copper trace layer but in another embodiment, additional portions of the copper trace layer are available for layering. The copper trace layer of the flexible ECG pad structure provides the electrical connection to the wearable sensor device.

After the copper trace layer has the ENIG cover and cover layer applied on top of the first and second portions respectively, the silver paste trace layer is provided to come in contact and be connected to the ENIG cover. The silver paste trace layer is provided by using a silk screen of a silver (Ag) paste trace that is applied to the vias at the contact area near the ENIG cover. The silver paste trace layer comprises both a connection portion and a pad portion.

In one embodiment, the pad portion is coupled to the connection portion and in another embodiment the silver paste trace layer is manufactured as one unit with the connection and pad portions merely denoting various regions of the silver paste trace layer. The pad portion can be a variety of shapes including but not limited to round, square, rectangular, oval, triangular, hexagonal, and polygonal.

In one embodiment, the pad portion of the silver paste trace layer also includes another intermediate layer of silver/silver chloride (Ag/AgCl) that is applied using a silk screen of AgCl paste that connects the AgCl paste to the Ag (coming through the vias) thereby providing the hydrogel contact pad area. The Ag/AgCl layer serves as a reference electrode that is an electrode which has a stable electrode potential. In another embodiment, vias are not utilized and the Ag/AgCl layer is silkscreened directly on the silver paste trace layer.

A hydrogel layer is then applied only to the pad portion of the silver paste trace layer and above the Ag/AgCl layer that has been silk screened on top. The silver paste trace layer comprises a connection portion that just includes the silver paste and further comprises a pad portion that includes the Ag/AgCl and hydrogel layers layered on top of the pad portion. The combination of the silver paste trace layer connection portion and the pad portion that includes the Ag/AgCl and hydrogel layers complete the silver paste contact and trace construct.

To describe the features of the present invention in more detail, refer now to the following description in conjunction with the accompanying Figures.

FIG. 1 illustrates a wireless sensor device 100 that utilizes a flexible circuit design that includes a flexible ECG pad structure in accordance with an embodiment. The wireless sensor device 100 ("wearable device") includes a sensor 102, a processor 104 coupled to the sensor 102, a memory 106 coupled to the processor 104, an application 108 coupled to the memory 106, and a transmitter 110 coupled to the application 108. One of ordinary skill in the art readily recognizes that the wireless sensor device 10 can include other components and that the components of the wireless sensor device 100 can be coupled in a variety of different ways and that would be within the spirit and scope of the present invention.

In one embodiment, the wireless sensor device 100 is attached to a user to detect various physiological signals including ECG related signals via the sensor 102. The sensor 102 obtains the physiological signal data from the user, which is transmitted to the memory 106 and in turn to the application 108 via the processor 104. The processor 104 executes the application 108 to process and analyze the data to obtain health-related information. The information is transmitted to the transmitter 110 and in turn relayed to another user or device for further processing, analysis, and storage. In another embodiment, the transmitter 110 transmits the various detected physiological signals in raw form to a remote device/server (e.g., smartphone, cloud-based server, etc.) for further processing, analysis, and storage.

In one embodiment, the sensor 102 is any of a microelectromechanical systems (MEMS) multi-axial (e.g., tri-axial) accelerometer, an embedded sensor with electrodes, and a photoplethysmography sensor. In one embodiment, the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect Health Patch® wearable device, electrocardiograph devices, smart watches, photoplethysmographs, pulse oximeters, tri-axial accelerometers, uni-axial accelerometers, bi-axial accelerometers, gyroscopes, and pressure sensors and that would be within the spirit and scope of the present invention.

In one embodiment, the HealthPatch® wearable device is a disposable adhesive patch biosensor worn on the chest that incorporates two surface electrodes with hydrogel on the bottom, a battery, an electronic module with an embedded processor and other electronic components and circuitry, a MEMS tri-axial accelerometer, and a Bluetooth Low Energy (BLE) transceiver.

In one embodiment, the wearable device facilitates continuous and automated monitoring of a plurality of physiological signals. In this embodiment, after the wearable device detects the plurality of physiological signals via a plurality of internal and embedded sensors, the electronic module of the wearable device utilizes a plurality of algorithms (e.g., firmware algorithms) to process raw waveforms of the plurality of physiological signals and to transmit a stream of the processed physiological variables via the BLE transceiver/link as encrypted data to a relay such as a smartphone, where the live (real-time) streams of data can be viewed, stored, and analyzed.

Figure 2:
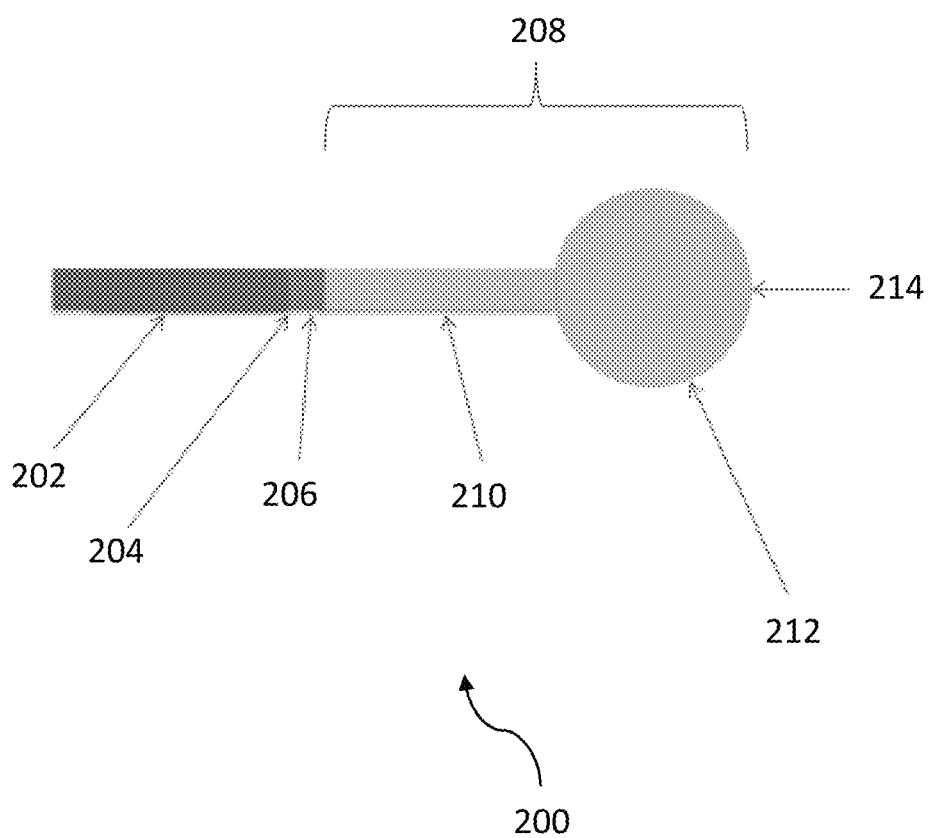
FIG. 2 illustrates a flexible ECG pad structure in accordance with an embodiment.

FIG. 2 illustrates a flexible ECG pad structure 200 in accordance with an embodiment. The flexible ECG pad structure 200 includes an underlying copper layer that has a cover layer 202 on top of a left-side portion of the underlying copper layer. The cover layer 202 has a predetermined length that can vary and reaches a certain point 204 that enables an opening above the underlying copper layer to be present. The width of the cover layer 202 mirrors and is substantially similar to the width of the underlying copper layer.

The flexible ECG pad structure 200 includes an ENIG cover 206 that is placed on top of the underlying copper layer and near the opening provided by the cover layer 202 that stops at the certain point 204. In addition, the flexible ECG pad structure 200 includes a paste trace layer 208 that comprises a connection portion 210 and a pad portion 212. In one embodiment, the paste trace layer 208 is silk screened onto the base polyimide base layer of the flexible ECG pad structure 200. In another embodiment, the paste trace layer 208 is applied onto the base polyimide base layer using a different manufacturing process. In one embodiment, the paste trace layer 208 is made of silver (Ag) and in another embodiment, the paste trace layer 208 is made of gold (Au). In another embodiment, the paste trace layer 208 is made from a mixture or combination of both silver and gold and other similar elements/materials.

The connection portion 210 comes in contact with the ENIG cover 206 (specifically, a portion of the connection portion 210 is coupled on top of the ENIG cover 206) which separates the underlying copper layer (with cover layer 202 and ENIG cover 206 both on top) from the rest of the flexible ECG pad structure 200 made from the silver (or gold or mixture) paste. The paste trace layer 208 spans the right side of the flexible ECG pad structure 200 whereas the underlying copper layer, cover layer 202, and ENIG cover 206 spans the opposite left side of the flexible ECG pad structure 200.

In one embodiment, the pad portion 210 of the paste trace layer 208 includes additional layers on top that firstly comprises a silver/silver chloride (Ag/AgCl) layer and secondly comprises a hydrogel layer on top of the Ag/AgCl layer. In another embodiment, a different type of layer or reference electrode other than Ag/AgCl is placed on top of the pad portion 212 of the paste trace layer 208 as long as the different type of layer can also ensure that the hydrogel (or similar substance) adheres properly while providing a solid electrical connection as the sensor within the wearable sensor device is sensing when the wearable sensor device is in contact with the user's body.

In one embodiment, the pad portion 210 is circular 214 in shape. In another embodiment, the pad portion 210 is a different shape including but not limited to round, square, rectangular, oval, triangular, hexagonal, and polygonal that enables a solid electrode connection with the user of the wearable sensor device.

Figure 3A:
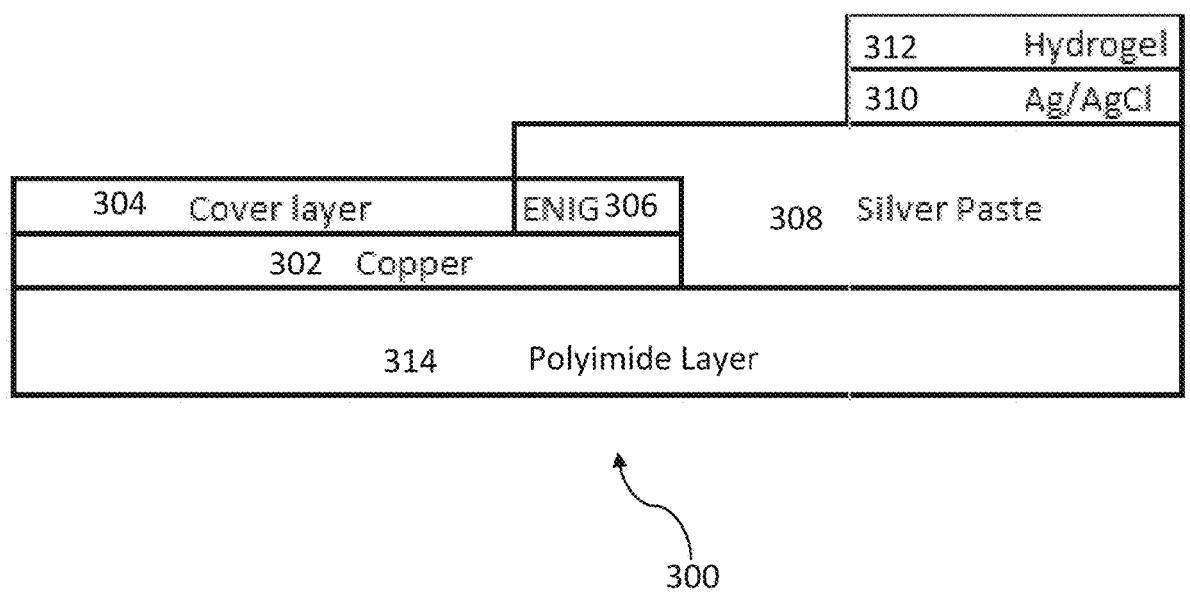
FIG. 3A illustrates a cross-section diagram of the flexible ECG pad structure in accordance with a first embodiment.

FIG. 3A illustrates a cross-section diagram of the flexible ECG pad structure 300 in accordance with a first embodiment. The flexible ECG pad structure 300 includes a base polyimide layer 314 with a copper layer 302 on top. The cover layer 302 has a cover layer 304 and an ENIG cover 306 on top. A silver paste trace layer 308 (that includes the connection portion and the pad portion) is placed on top of the ENIG cover 306 and also over the base polyimide layer 314. A Ag/AgCl layer 310 is placed on top of the pad portion (not shown) of the silver paste trace layer 308. A hydrogel layer 312 is placed directly on top of the Ag/AgCl layer 310. In another embodiment, the layers are stacked in slightly different orientations based upon various preferences. For example, instead of being directly layer on top, the hydrogel layer 312 can be housed within a certain section of the Ag/AgCl layer 310 or the Ag/AgCl layer 310 can span a greater distance across the silver paste trace layer 308 (so the proportions can vary).

Figure 3B:
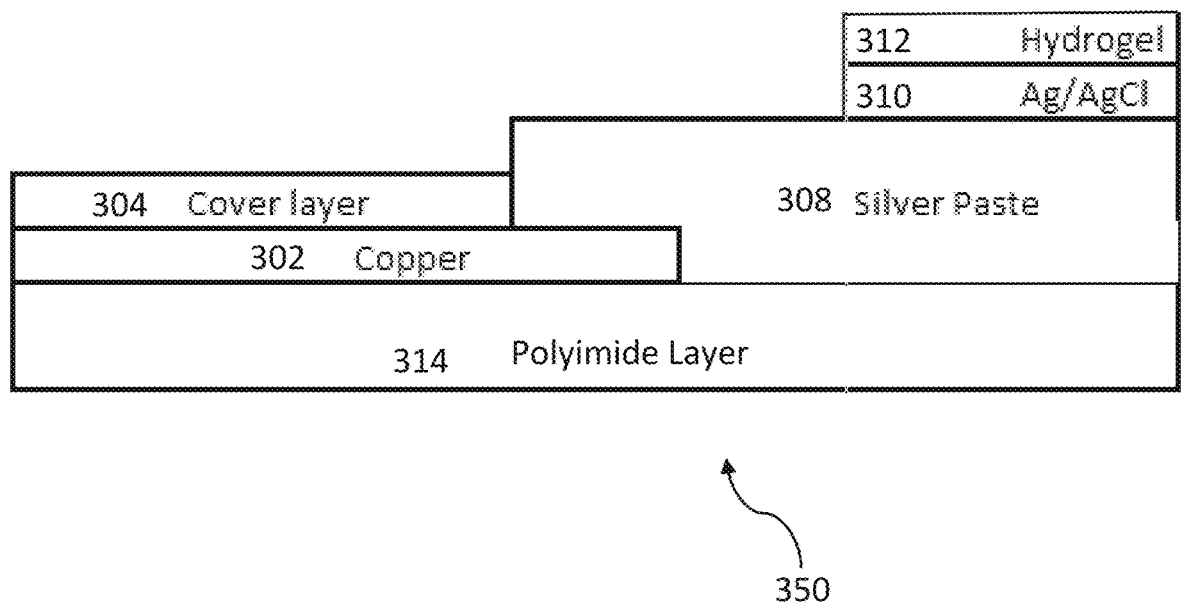
FIG. 3B illustrates a cross-section diagram of the flexible ECG pad structure in accordance with a second embodiment.

FIG. 3B illustrates a cross-section diagram of the flexible ECG pad structure 350 in accordance with a second embodiment. The flexible ECG pad structure 350 resembles the flexible ECG pad structure 300 and has all of the similar components except that it does not include an ENIG cover. Therefore, in the flexible ECG pad structure 350, the silver paste trace layer 308 is directly in contact with a top portion of the copper layer 302 and partially adjacent to the cover layer 304.

Figure 4:
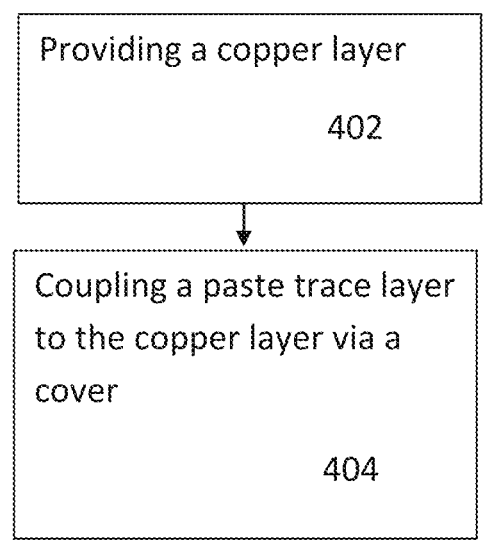
FIG. 4 illustrates a method for providing a flexible ECG pad structure in accordance with an embodiment.
Figure 4:

FIG. 4 illustrates a method 400 for providing a flexible electrocardiogram (ECG) pad structure in accordance with an embodiment. The method 400 comprises providing a copper layer and coupling a paste trace layer to the copper layer via a cover. In one embodiment, the cover is an electroless nickel immersion gold (ENIG) cover that is coupled on top of a first portion of the copper layer and is coupled on bottom of a first portion of the paste trace layer. In another embodiment, no cover layer is used and the paste trace layer is directly coupled to the copper layer. In this embodiment, the method further comprises coupling a cover layer on top of a second portion of the copper layer, wherein the cover layer and the ENIG cover entirely span a top surface of the copper layer.

In one embodiment, the paste trace layer is a silver (Ag) paste trace layer and is coupled to the copper layer via a first silk screening process. In another embodiment, the paste trace layer is coupled to the copper layer via a non-silk screening process. The method further comprises coupling an intermediate layer on top of a second portion of the paste trace layer, wherein the intermediate layer is coupled to the second portion of the paste trace layer via a second silk screening process. In one embodiment, the first and the second silk screening processes are similar and in another embodiment, the first and second silk screening processes are different.

After the intermediate layer is coupled to the second portion of the paste trace layer, the method further comprises coupling a hydrogel layer on top of the intermediate layer. The second portion of the paste trace layer is a pad portion and the method further comprises forming the pad portion into a predetermined shape that comprises any of circular, oval, square, rectangular, triangular, hexagonal, and polygonal.

The method provides a flexible ECG pad structure and system. Therefore, the system comprises a copper layer and a paste trace layer coupled to the copper layer via a cover. The copper layer is situated under or beneath the paste trace layer. In one embodiment, the cover is an electroless nickel immersion gold (ENIG) cover and in another embodiment, the cover is a different material with similar surface plating properties as ENIG.

In one embodiment, the ENIG cover is situated between the copper layer and the paste trace layer, and more specifically, the ENIG cover is coupled on top of a first portion of the copper layer and is coupled on bottom of a first portion of the paste trace layer. A cover layer is coupled on top of a second portion of the copper layer, wherein the cover layer and the ENIG cover entirely span a top surface of the copper layer. In another embodiment, the cover layer and ENIG cover only cover a portion of the copper layer and so a portion of the copper layer could be exposed and/or coupled to a different type of layer.

In one embodiment, the paste trace layer is made of any of silver (Ag), gold (Au), and a combination thereof. An intermediate layer is coupled on top of a second portion of the paste trace layer. In one embodiment, the intermediate layer serves as a reference electrode that is made of silver/silver chloride (Ag/AgCl) and is situated between the paste trace layer and a hydrogel layer that is coupled on top of the intermediate layer. In one embodiment, the hydrogel layer completely spans across the entire top surface of the intermediate layer but in another embodiment, only certain portions of the intermediate layer are covered by the hydrogel.

In one embodiment, the second portion of the paste trace layer forms a pad portion of the paste trace layer (i.e., where the electrode of the wearable sensor device comes in contact with the user) and a third portion of the paste trace layer is uncovered (nothing or no layers are coupled on top of this portion). The second portion combines with the first portion (that is connected to the ENIG cover) to form a connection portion of the paste trace layer. The connection portion separates the pad portion from the copper layer thereby mitigating against CuCl2 corrosion issues. The pad portion is formed in a predetermined shape that includes but is not limited to any of circular/round, oval, square, rectangular, triangular, hexagonal, and polygonal.

As above described, a system and method in accordance with the present invention provide for a flexible electrocardiogram (ECG) pads (and pad structure) that mitigate against corrosion issues typically found in conventional ECG pads that comprise copper flex technology throughout the structure and the design. By utilizing an ENIG cover that is situated between the underlying copper layer and the overlying paste trace layer (e.g., silver paste) layer, the hydrogel portion of the ECG pad is situated away from any copper portions of the device thereby eliminating the possibility of hydrogel ion migration and contact with the copper which leads to the CuCl2 corrosion issues that encompass cosmetic and shelf-life issues.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A flexible electrocardiogram pad, comprising:
    a copper layer having a skin facing side and a non-skin facing side, wherein the skin facing side includes a first portion and a second portion;
    a cover which covers the second portion of the skin facing side of the copper layer;
    an electroless nickel immersion gold (ENIG) cover coupled to the first portion of the copper layer; and
    a paste trace layer having a skin facing side and a non-skin facing side,
    wherein the paste trace layer comprises a connection portion and a pad portion;
    wherein the ENIG cover is coupled on bottom of the connection portion of the non-skin facing side of the paste trace layer;
    the connection portion of the non-skin facing side of the paste trace layer is coupled to the skin facing side of the copper layer via the ENIG cover; and
    the pad portion of the paste trace layer is in contact with the copper layer.

2. The flexible electrocardiogram pad of claim 1, wherein the cover and the ENIG cover span the entire surface of the copper layer on the skin facing side.

3. The flexible electrocardiogram pad of claim 1, wherein the skin facing side of the paste trace layer is coupled to a layer made of any of silver (Ag), gold (Au), or a combination thereof.

4. The flexible electrocardiogram pad of claim 1, wherein the pad portion of the paste trace layer on the skin facing side is a second portion of the paste trace layer, wherein an intermediate layer is coupled to the second portion of the paste trace layer.

5. The flexible electrocardiogram pad of claim 4, wherein the intermediate layer is a reference electrode that is made of silver/silver chloride (Ag/AgCl).

6. The flexible electrocardiogram pad of claim 4, wherein a hydrogel layer is disposed on top of the intermediate layer.

7. The flexible electrocardiogram pad of claim 4, wherein the connection portion of the paste trace layer is a first portion of the paste trace layer, wherein a third portion of the paste trace layer is uncovered and combines with the first portion of the paste trace layer.

8. The flexible electrocardiogram pad of claim 7, wherein the pad portion is in a predetermined shape.

9. The flexible electrocardiogram pad of claim 8, wherein the predetermined shape is any of circular, oval, square, rectangular, triangular, hexagonal, and polygonal.

10. A method for providing a flexible electrocardiogram (ECG) pad structure, the method comprising:
    providing a copper layer having a skin facing side and a non-skin facing side, wherein the skin facing side includes a first portion and a second portion;
    providing a cover which covers the second portion of the skin facing side of the copper layer;
    providing an electroless nickel immersion gold (ENIG) cover coupled to the first portion of the copper layer; and
    providing a paste trace layer having a skin facing side and a non-skin facing side,
    wherein the paste trace layer comprises a connection portion and a pad portion;
    wherein the ENIG cover is coupled on bottom of the connection portion of the non-skin facing side of the paste trace layer;
    coupling the connection portion of the non-skin facing side of the paste trace layer to the skin facing side of the copper layer via the ENIG cover; and coupling the pad portion of the paste trace layer to the copper layer.

11. The method of claim 10, wherein the cover and the ENIG cover span the entire top surface of the copper layer.

12. The method of claim 10, wherein the paste trace layer is coupled to the copper layer via a first silk screening process.

13. The method of claim 12, further comprising: coupling an intermediate layer on top of the pad portion of the paste trace layer, wherein the intermediate layer is coupled to the pad portion of the paste trace layer via a second silk screening process.

14. The method of claim 13, further comprising:
    coupling a hydrogel layer on top of the intermediate layer.

15. The method of claim 13, forming the pad portion of the paste trace layer into a predetermined shape, wherein the predetermined shape is any of circular, oval, square, rectangular, triangular, hexagonal, and polygonal.

* * * * *